US 010407656B2

(12) United States Patent
Cui et al.

(10) Patent No.: US 10,407,656 B2
(45) Date of Patent: *Sep. 10, 2019

(54) CELL CULTURE AND EXPERIMENT DEVICE

(71) Applicant: GUANGZHOU INSTITUTE OF ADVANCED TECHNOLOGY, CHINESE ACADEMY OF SCIENCES, Guangzhou, Guangdong (CN)

(72) Inventors: Jinming Cui, Guangdong (CN); Shijie Zeng, Guangdong (CN); Olaf Eichstaedt, Guangdong (CN); Jiandong Huang, Guangdong (CN); Ruxu Du, Guangdong (CN); Hai Yuan, Guangdong (CN)

(73) Assignee: GUANGZHOU INSTITUTE OF ADVANCED TECHNOLOGY, CHINESE ACADEMY OF SCIENCES, Guangzhou (CN)

( * ) Notice: Subject to any disclaimer, the term of this patent is extended or adjusted under 35 U.S.C. 154(b) by 297 days.

This patent is subject to a terminal disclaimer.

(21) Appl. No.: 15/275,503

(22) Filed: Sep. 26, 2016

(65) Prior Publication Data

US 2017/0009196 A1    Jan. 12, 2017

Related U.S. Application Data

(63) Continuation of application No. PCT/CN2014/075210, filed on Apr. 11, 2014.

(30) Foreign Application Priority Data

Mar. 25, 2014    (CN) .......................... 2014 1 0112722

(51) Int. Cl.
  *C12M 3/00*    (2006.01)
  *C12M 1/42*    (2006.01)
  (Continued)

(52) U.S. Cl.
  CPC ............ *C12M 23/42* (2013.01); *C12M 23/34* (2013.01); *C12M 23/40* (2013.01); *C12M 29/04* (2013.01);
  (Continued)

(58) Field of Classification Search
  CPC ...... C12M 23/42; C12M 23/34; C12M 23/40; C12M 29/04; C12M 35/02; C12M 41/36; C12M 41/46
  See application file for complete search history.

(56) References Cited

U.S. PATENT DOCUMENTS

2005/0175273 A1*   8/2005   Iida ................... B01L 3/502715
                                                              385/15
2017/0130183 A1*   5/2017   Cui ........................ C12M 29/04

FOREIGN PATENT DOCUMENTS

CN        101730564 A      6/2010
CN        102378945 A      3/2012
  (Continued)

OTHER PUBLICATIONS

International Search Report of PCT Patent Application No. PCT/CN2014/075210 dated Jan. 8, 2015.
  (Continued)

*Primary Examiner* — Michael L Hobbs

(57) ABSTRACT

The invention discloses a cell culture and experiment device used in the field of biological and genetic engineering experiment apparatus, comprising a cent distribution compartment, a culture compartment, a treatment compartment, and pipelines for delivering liquid between the central distribution compartment and the culture compartment and between the central distribution compartment and the treatment compartment. The central distribution compartment is equipped with a distribution chamber and a piston which can be moved forward and backward in the distribution chamber to alter the working volume of the distribution chamber. At the bottom of the distribution chamber, the central distribution compartment is equipped with a distribution valve
  (Continued)

controlling the connectivity between the distribution chamber and any of the channels. The invention provides a miniaturized apparatus integrating the central distribution compartment, the culture compartment and the treatment compartment, which can replace manual operations, save time and labor, and avoid wasting experimental raw material.

9 Claims, 14 Drawing Sheets

(51) Int. Cl.
    *C12M 1/00*         (2006.01)
    *C12M 1/34*         (2006.01)

(52) U.S. Cl.
    CPC ............ *C12M 35/02* (2013.01); *C12M 41/36* (2013.01); *C12M 41/46* (2013.01)

(56) References Cited

FOREIGN PATENT DOCUMENTS

| CN | 103370409 A | 10/2013 | |
|---|---|---|---|
| WO | 0218902 A1 | 3/2002 | |
| WO | WO-0218902 A1 * | 3/2002 | .............. B01L 3/502 |

OTHER PUBLICATIONS

1st Office Action of counterpart Chinese Patent Application No. 201410112722.6 dated Feb. 11, 2015.

\* cited by examiner

E-E

CELL CULTURE AND EXPERIMENT DEVICE

CROSS REFERENCE TO RELATED APPLICATIONS

This application is a continuation application of a PCT application No. PCT/CN2014/075210, filed on Apr. 11, 2014, which claims priority to Chinese Patent Application No. 201410112722.6, filed on Mar. 25, 2014, the entire contents of which are incorporated herein by reference.

TECHNICAL FIELD

The disclosure is applied to the field of biological and genetic engineering experiment devices, and particularly relates to a cell culture and experiment device.

BACKGROUND

In the field of microbiology, particularly the fields of biological engineering, genetic engineering and the like, researchers execute experiment operations using cultured cells so as to verify their theories and experiments. These basic experiment operations include, but are not limited to, 1, culturing cells, particularly reproducing the cells in a liquid culture medium determined by one or more components;

2, measuring cell density;

3, separating the cells from the liquid culture medium;

4, re-suspending the cells using fresh liquid;

5, operating the cells by means of a chemical way, an electric way or other physical ways, for example, introducing genetic materials such as plasmids or oligonucleotides;

6, sterilizing an instrument using alcohol or other solutions; and 7, cleaning the instrument using water.

A current mainstream experiment flow refers to sequentially completing the above steps in small batches by means of manual operations. Commonly used traditional experiment instruments include: a test tube, a shake flask, a shaker, a culture dish, a cuvette, an injector, a pipettor, a centrifugal machine, a filter membrane and the like. When multiple turns of experiment operations or experiment operations on a plurality of samples are executed, it is necessary to consume a great amount of time and labour.

Although a certain degree of automation can be obtained by combining traditional instruments into a mini plant and adding a control assembly, the solution has the defects that each traditional instrument is not designed for combination, mutual specifications do not match, the combined mini plant is too large for a traditional biochemical laboratory, and a relatively large amount of needed cell culture fluid will make raw experimental materials too expensive.

SUMMARY

To solve the above problems, the disclosure provides a small cell culture and experiment device which takes the place of manual operation, is capable of completing various experimental projects, saves time and labour and avoids waste of raw experimental materials.

To solve the technical problem, the disclosure adopts the technical solution as follows. A cell culture and experiment device may include a central distribution compartment, a culture compartment, a treatment compartment, and pipelines for delivering liquid between the central distribution compartment and the culture compartment and between the central distribution compartment and the treatment compartment, wherein a distribution chamber and a piston capable of moving back and forth in the distribution chamber to change the working volume of the distribution chamber are provided in the central distribution compartment, and a distribution valve for controlling the distribution chamber to be communicated with any pipeline is arranged at the bottom end of the distribution chamber in the central distribution compartment.

Furthermore, as an improvement of the technical solution of the disclosure, the central distribution compartment, the culture compartment and the treatment compartment may be arranged separately, the central distribution compartment may surround the distribution valve to form a plurality of mounting surfaces which can be connected to the culture compartment or the treatment compartment, a central pipeline leading from the distribution valve to each mounting surface may be arranged on the central distribution compartment, the distribution valve may include a central cylinder hole provided at the bottom end of the distribution chamber and a central valve element which is inserted into the central cylinder hole and can rotate in the central cylinder hole, a central flow channel may be provided on the central valve element, and when the central valve element rotates, the central flow channel may communicate the distribution chamber with any central pipeline.

Furthermore, as an improvement of the technical solution of the disclosure, the culture compartment may include a culture chamber formed by a cylindrical outer wall and a plug arranged at the front end of the outer wall, and a multi-way valve arranged at the rear end of the outer wall. An air hole may be provided on the plug. The multi-way valve may include a first standard shape block which can be connected to the mounting surfaces and is provided with a cylinder hole and a pipeline, and a first valve element which is inserted into the cylinder hole and can rotate in the cylinder hole. A first connector may be arranged on the first standard shape block. A first flow channel may be provided on the first valve element. When the first valve element rotates, the first flow channel may communicate the first connector with the culture chamber by means of the pipeline or communicate the first connector with the distribution valve or communicate the culture chamber with the distribution valve.

Furthermore, as an improvement of the technical solution of the disclosure, the outer side of the outer wall may be sheathed by a sleeve, a cavity may be formed between the sleeve and the outer wall, an outlet and an inlet communicated with the cavity may be formed at the front end and rear end of the sleeve, and a spiral partition wall may be arranged in the cavity so as to form a channel which surrounds the outer wall and is connected to the outlet and the inlet.

Furthermore, as an improvement of the technical solution of the disclosure, a spiral guide pipe may surround the outer wall, and the inner diameter of the spiral guide pipe may be smaller than the outer diameter of the culture chamber.

Furthermore, as an improvement of the technical solution of the disclosure, the treatment compartment may include an electric treatment compartment, the electric treatment compartment may include a second standard shape block which is provided with a pipeline and can be connected to the mounting surfaces, two electrodes may face two sides of the pipeline in the middle of the second standard shape block, electric connectors which can be connected to external power supplies or measurers may be arranged at the outer ends of the two electrodes, an insulating partition sheet may be arranged between the two electrodes in the pipeline, and the insulating partition sheet may form a protrusion controlling liquid to flow through the pipeline.

Furthermore, as an improvement of the technical solution of the disclosure, the treatment compartment may include a first filter compartment, the first filter compartment may include a third standard shape block which is provided with a pipeline and can be connected to the mounting surfaces, a filter device which divides the pipeline into a front section and a rear section may be arranged in the third standard shape block, the filter device may include a filter membrane and a porous member arranged at the rear side of the filter membrane, the third standard shape block may include a front half part and a rear half part which can be assembled into a whole, an inner chamber for accommodating the filter device may be formed between the front half part and the rear half part, a first spiral guide groove may be formed in the end surface, tightly attached to the filter membrane, of the front half part, and a first port for injecting external liquid may be formed for the first guide groove on the side surface of the front half part.

Furthermore, as an improvement of the technical solution of the disclosure, the treatment compartment may include a second filter compartment, the second filter compartment may include a fourth standard shape block which is provided with a pipeline and can be connected to the mounting surfaces, an inner filter chamber communicated with a pipeline may be formed inside the fourth standard shape block, an end cap which is hermetically connected to the fourth standard shape block and is internally provided with a pipeline may be arranged at the tail end of the inner filter chamber, a fibre filter membrane extending into the inner filter chamber may be arranged at the inner end of the end cap, a second port communicated with the inner filter chamber may be provided on the side wall of the fourth standard shape block, and the second port may lead into the inner filter chamber along a tangential direction.

Furthermore, as an improvement of the technical solution of the disclosure, a second spiral guide groove may be provided on the inner wall of the inner filter chamber, and the second guide groove and the second port may be connected and may surround the fibre filter membrane.

Furthermore, as an improvement of the technical solution of the disclosure, the treatment compartment may include a cell density measurement compartment, the cell density measurement compartment may include a fifth standard shape block which is provided with a pipeline and can be connected to the mounting surfaces, an optical channel transversely penetrating through the pipeline may be provided on the fifth standard shape block, a light source and a light sensor may be arranged at two ends of the optical channel respectively, and transparent waveguide elements may be arranged on two sides of the pipeline between the light source and the light sensor.

Furthermore, as an improvement of the technical solution of the disclosure, an optical channel transversely penetrating through the distribution chamber may be provided on the central distribution compartment, a light source and a light sensor may be arranged at two ends of the optical channel respectively, and transparent waveguide elements may be arranged on two sides of the distribution chamber between the light source and the light sensor.

The disclosure has the beneficial effects as follows. The cell culture and experiment device includes at least one culture compartment, a central distribution compartment including a piston and a distribution valve, at least one treatment compartment, and a series of pipelines for delivering liquid between the compartments.

When in use, cells grow and reproduce in the culture compartment firstly. A cell suspension can be delivered to the treatment compartment from the culture compartment by selecting a distribution valve passage and moving the piston in the distribution chamber. Treatment operations including optical density measurement, cell and culture solution separation, conductivity measurement, electric transformation, temperature rise, temperature reduction and electromagnetic radiation are further completed in the treatment compartment.

By means of the above design, the disclosure provides a small device integrating a central distribution compartment, a culture compartment and a treatment compartment, thereby taking the place of manual operation while completing cell culture and various experimental projects, saving time and labour, avoiding waste of raw experimental materials, and reducing an opportunity of exposing experimenters under harmful substances.

BRIEF DESCRIPTION OF THE DRAWINGS

The disclosure is further illustrated below in conjunction with the drawings.

DETAILED DESCRIPTION OF THE EMBODIMENTS

Figure 1:
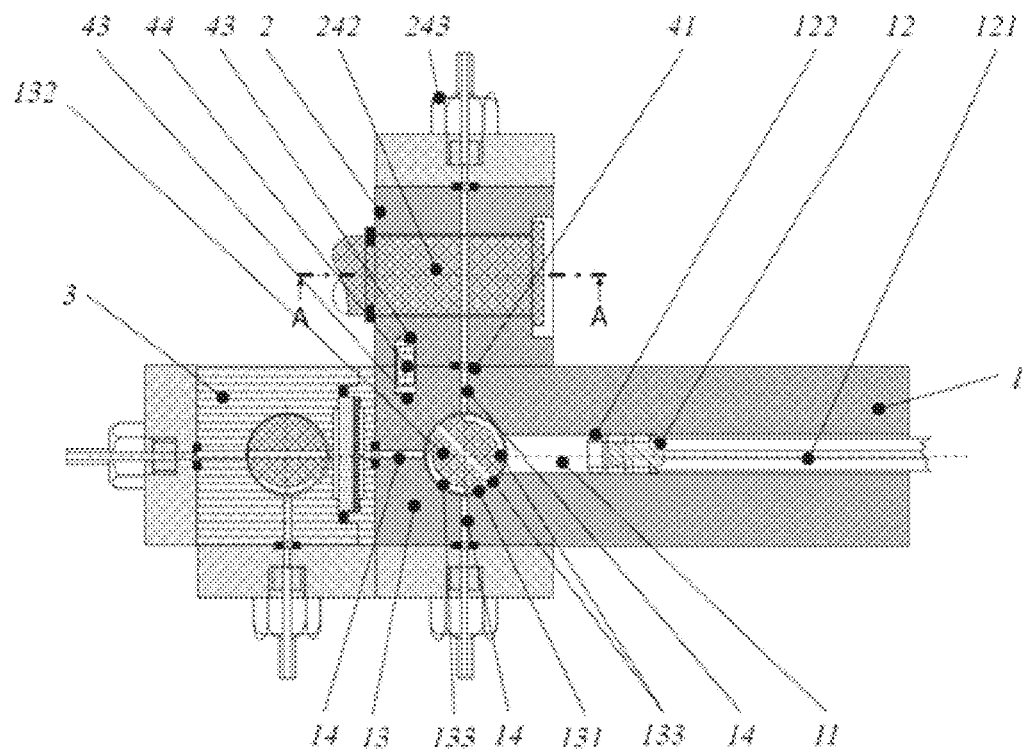
FIG. 1 is a basic structure diagram of an embodiment of the disclosure.

With reference to FIG. 1 to FIG. 22, the disclosure provides a cell culture and experiment device, which includes a central distribution compartment 1, a culture compartment 2, a treatment compartment 3, and pipelines 4 for delivering liquid between the central distribution compartment 1 and the culture compartment 2 and between the central distribution compartment 1 and the treatment compartment 3, wherein a distribution chamber 11 and a piston 12 capable of moving back and forth in the distribution chamber 11 to change the working volume of the distribution chamber 11 are provided in the central distribution compartment 1, and a distribution valve 13 for controlling the distribution chamber 11 to be communicated with any pipeline 4 is arranged at the bottom end of the distribution chamber 11 in the central distribution compartment 1.

With reference to FIG. 1, the central distribution compartment 1, the culture compartment 2 and the treatment compartment 3 are arranged separately, the central distribution compartment 1 surrounds the distribution valve 13 to form a plurality of mounting surfaces which can be connected to the culture compartment 2 or the treatment compartment 3, three central pipelines 14 leading from the distribution valve 13 to three mounting surfaces are arranged on the central distribution compartment 1, the distribution valve 13 includes a central cylinder hole 131 provided at the bottom end of the distribution chamber 11 and a central valve element 132 which is inserted into the central cylinder hole 131 and can rotate in the central cylinder hole 131, a central flow channel 133 is provided on the central valve element 132, and when the central valve element 132 rotates, the central flow channel 133 can communicate the distribution chamber 11 with any central pipeline 14.

Figure 2:
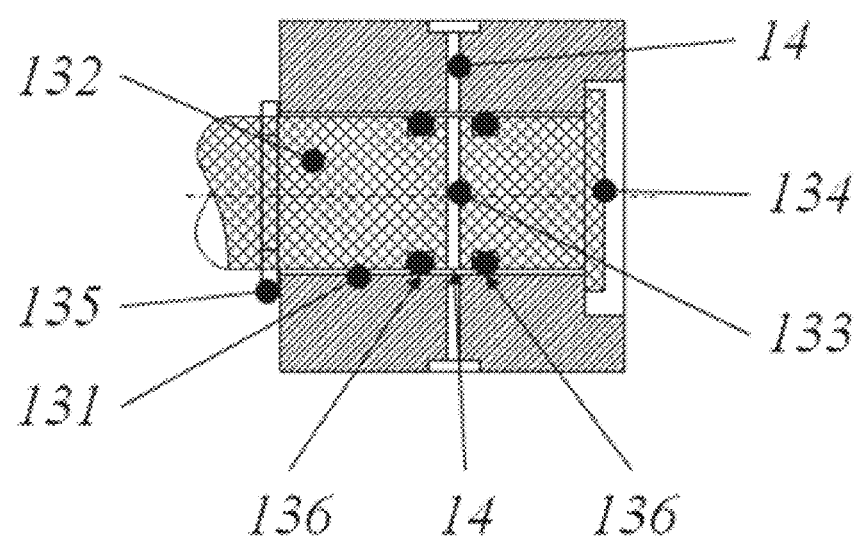
FIG. 2 is a structural diagram of a distribution valve in an embodiment of the disclosure.
Figure 3:
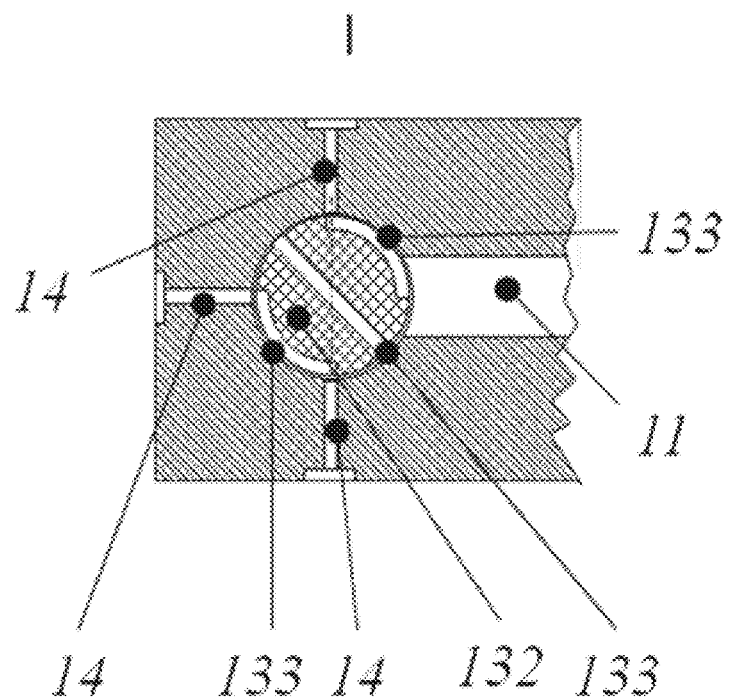
FIG. 3 is a structural diagram illustrating that a valve element rotates to a position I in an embodiment of the disclosure.
Figure 4:
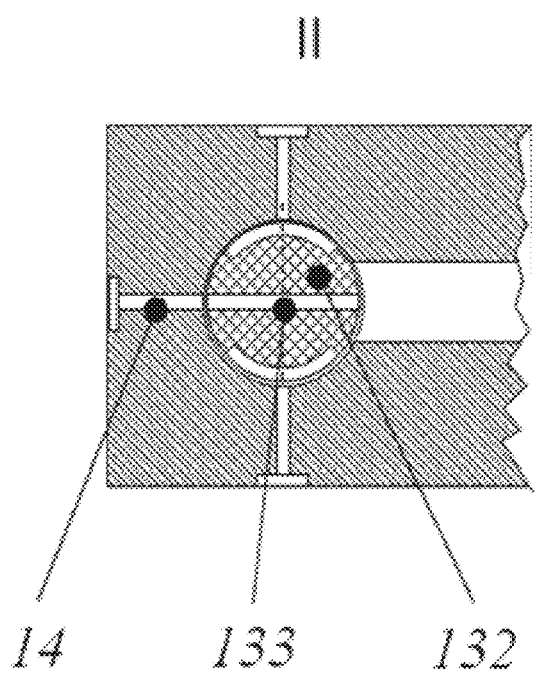
FIG. 4 is a structural diagram illustrating that a valve element rotates to a position II in an embodiment of the disclosure.
Figure 5:
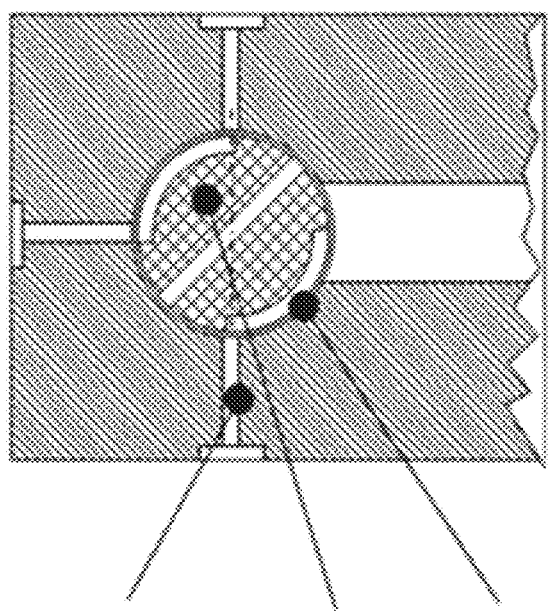
FIG. 5 is a structural diagram illustrating that a valve element rotates to a position III in an embodiment of the disclosure.
Figure 6:
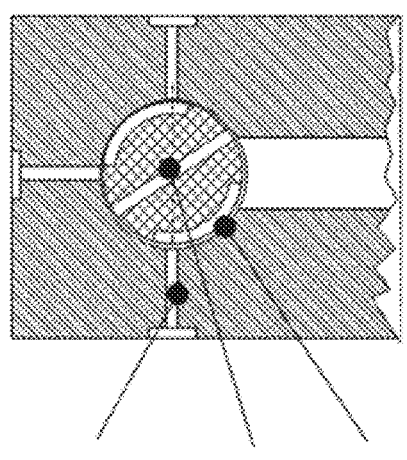
FIG. 6 is a structural diagram illustrating that a valve element rotates to a position III' in an embodiment of the disclosure.
Figure 7:
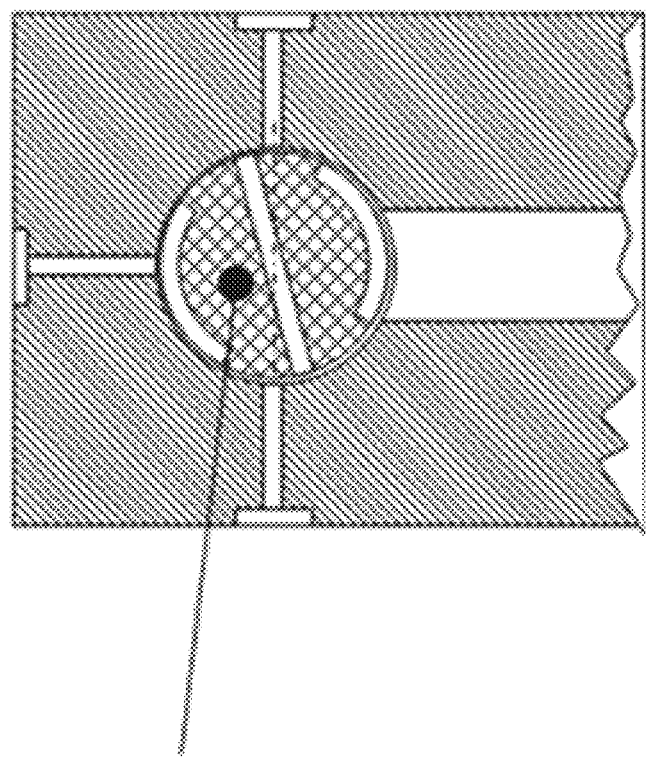
FIG. 7 is a structural diagram illustrating that a valve element rotates to a position IV in an embodiment of the disclosure.

With reference to FIG. 2, a protrusion 134 is arranged at one end of the central valve element 132 of the distribution valve 13, and a fixed element 135 (for example, a Seeger clamping ring or a coil spring) is arranged at the other end of the central valve element 132 and configured to fix the central valve element 132 to a specific axial direction of the central cylinder hole 131. Obviously, the fixed element 135 may take the place of the protrusion 134 for fixing the axial direction.

The central flow channel 133 on the central valve element 132 may be of different shapes. For example, the central flow channel 133 may pass through the central valve element 132 so as to be connected to the central pipelines 14, two ends facing the central pipelines 14. The central flow channel 133 is located on the periphery of the central valve element 132 and is configured to be connected to the adjacent central pipelines 14. In the present embodiment, an angle between the adjacent central pipelines 14 is 90 degrees. By adjusting the length of the central flow channel 133, the central flow channel 133 may adapt to an included angle of smaller than or greater than 90 degrees.

Two first elastic sealing elements 136 are arranged on two sides of the central flow channel 133 on the central valve element 132 and are configured to prevent liquid from leaking along the long axis of the central valve element 132.

FIGS. 3-7 illustrate four working positions of the distribution valve 13. When the central valve element 132 rotates to a position I, the culture compartment 2 is connected to the distribution chamber 11. The treatment compartment 3 is communicated with the lower central pipeline 14, and liquid can be delivered by means of an external pump.

When the central valve element 132 rotates to a position II, the distribution chamber 11 is connected to the treatment compartment 3, and the upper and lower central pipelines 14 are closed.

When the central valve element 132 rotates to a position III, the culture compartment 2 is connected to the treatment compartment 3, and the distribution chamber 11 is connected to the lower central pipeline 14. It is important to note that when the central valve element 132 is at the position III, if it is not desired that the culture compartment 2 is connected to the treatment compartment 3, the position III may be switched to a position III'. The distribution chamber 11 is different from the central pipelines 14 in diameter, the distribution chamber 11 may be connected to the lower central pipeline 14, and meanwhile, the culture compartment 2 and the treatment compartment 3 keep closed.

When the central valve element 132 rotates to a position IV, the central pipelines 14 and the distribution chamber 11 are completely separated from each other, which may be applied to a standby mode of the device.

Obviously, other valves with different characteristics may also be obtained by means of other combinations of the central pipelines 14.

In the disclosure, the piston 12 is inserted into the distribution chamber 11 in the central distribution compartment 1 and can move back and forth, and the piston 12 is connected to a linear drive device (omitted in the drawings) by means of a rigid part 121 and is connected with an elastic part 122. The elastic part 122 is attached to the front end of the rigid part 121 and can move along an axial direction of the distribution chamber 11. The design is commonly used for an injector and an injection pump. When the design is used for the device of the disclosure, three advantages are provided as follows.

(i) While the piston 12 moves along an inner wall of the distribution chamber 11, the inner wall can be cleaned. The self-cleaning characteristic eliminates additional cleaning steps, such that the same central distribution compartment 1 can be used during treatment of various kinds of liquid.

(ii) Liquid, suspensions containing cells, gas and the like can be absorbed or pushed.

(iii) The linear movement of the piston 12 can be easily converted into volume, flow and the like by utilizing the cross section area of the distribution chamber 11.

In addition, the distribution valve 13 is directly connected to the distribution chamber 11, and when different steps are carried out, the quantity of residual liquid between the distribution chamber 11 and the distribution valve 13 is minimized.

Figure 8:
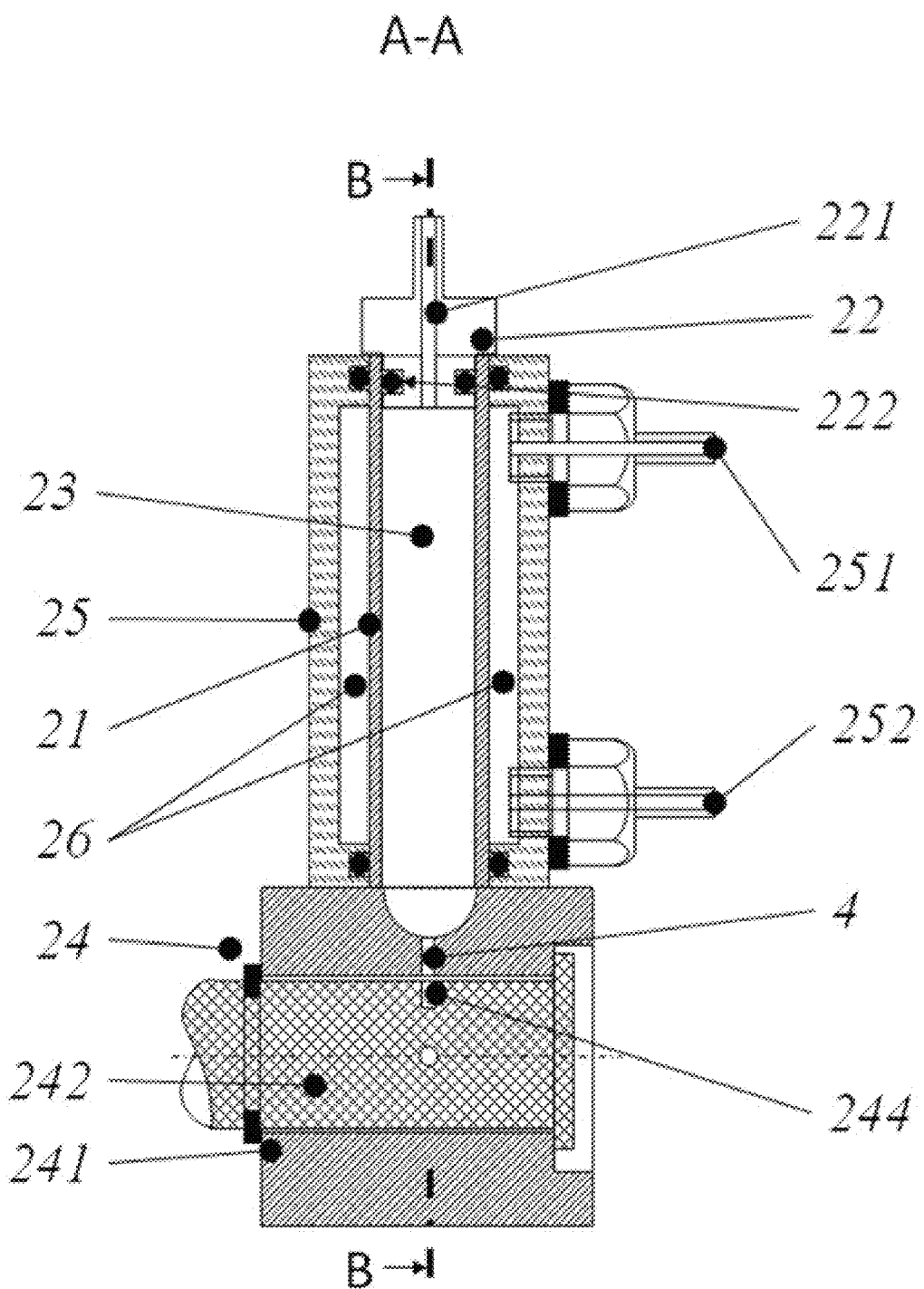
FIG. 8 is a section view of a part A-A in FIG. 1.
Figure 9:
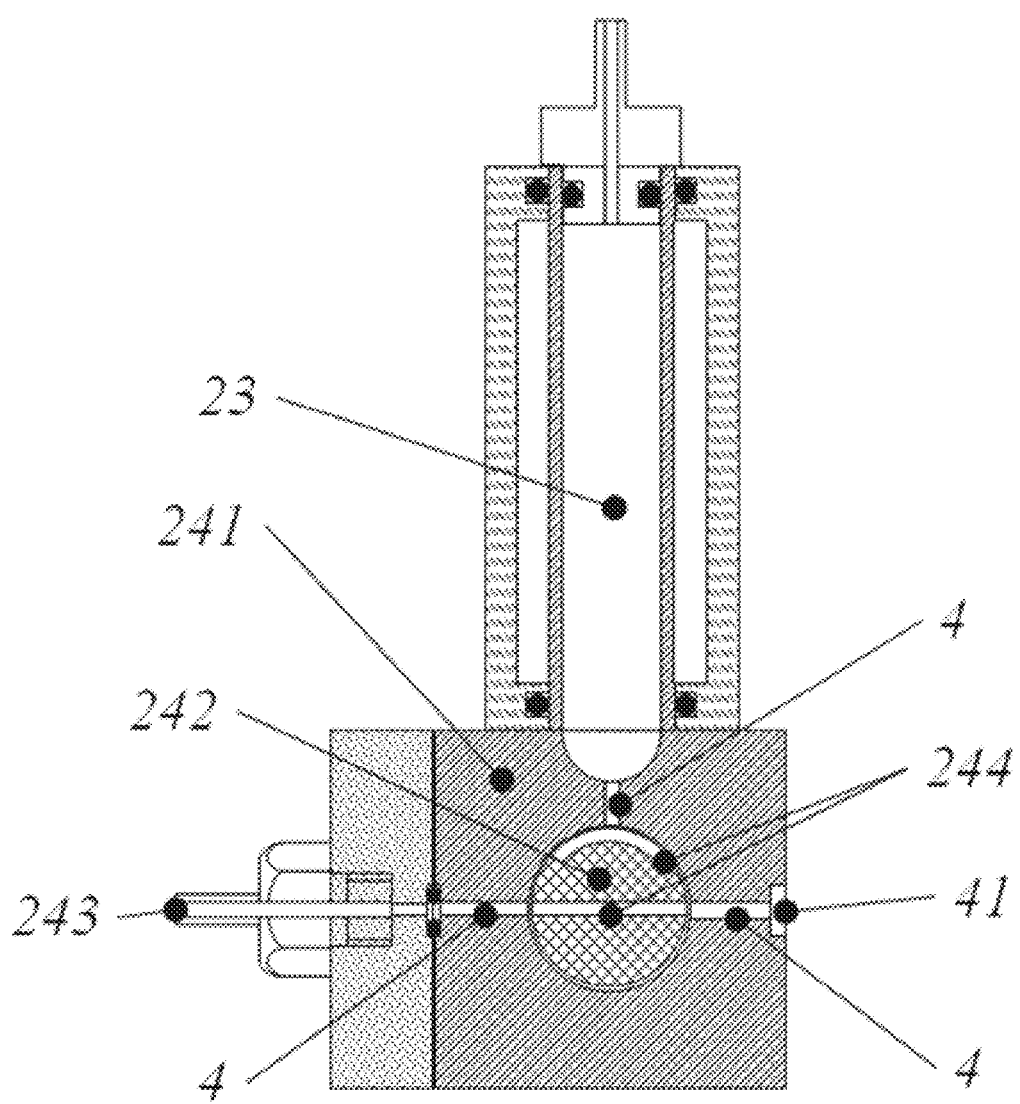
FIG. 9 is a section view of a part B-B in FIG. 8.

With reference to FIG. 8 and FIG. 9, the culture compartment 2 includes a culture chamber 23 formed by a cylindrical outer wall 21 and a plug 22 arranged at the front end of the outer wall 21, and a multi-way valve 24 arranged at the rear end of the outer wall 21. An air hole 221 is provided on the plug 22. The plug 22 seals the outer wall 21 using a second elastic sealing element 222. The multi-way valve 24 is similar to the distribution valve 13 in design, and includes a first standard shape block 241 which can be connected to the mounting surfaces and is provided with a cylinder hole and a pipeline 4, and a first valve element 242 which is inserted into the cylinder hole and can rotate in the cylinder hole. A first connector 243 is arranged on the first standard shape block 241. A first flow channel 244 is provided on the first valve element 242. When the first valve element 242 rotates, the first flow channel 244 can isolate the culture chamber 23, or communicate the culture chamber 23 with the distribution valve 13 or connect the culture chamber 23 to the first connector 243 by means of the pipeline 4. If air is charged into the culture chamber 23 from the first connector 243, generated bubbles will supply oxygen to cells in the culture chamber 23, and meanwhile, a culture solution is stirred and mixed uniformly.

In order to control the metabolism and growth rate of cells, the outer side of the outer wall 21 is sheathed by a sleeve 25, a cavity 26 is formed between the sleeve 25 and the outer wall 21, and an outlet 251 and an inlet 252 communicated with the cavity 26 are formed at the front end and rear end of the sleeve 25. Cooled or heated liquid can be charged into the formed cavity 26, and the liquid enters or exits from the cavity 26 through the outlet 251 and the inlet 252. In order to improve heat conduction, a spiral partition wall can be arranged in the cavity 26 so as to form a channel which surrounds the outer wall 21 and is connected to the outlet 251 and the inlet 252 so as to guide the liquid to flow (omitted in the drawings).

Figure 10:
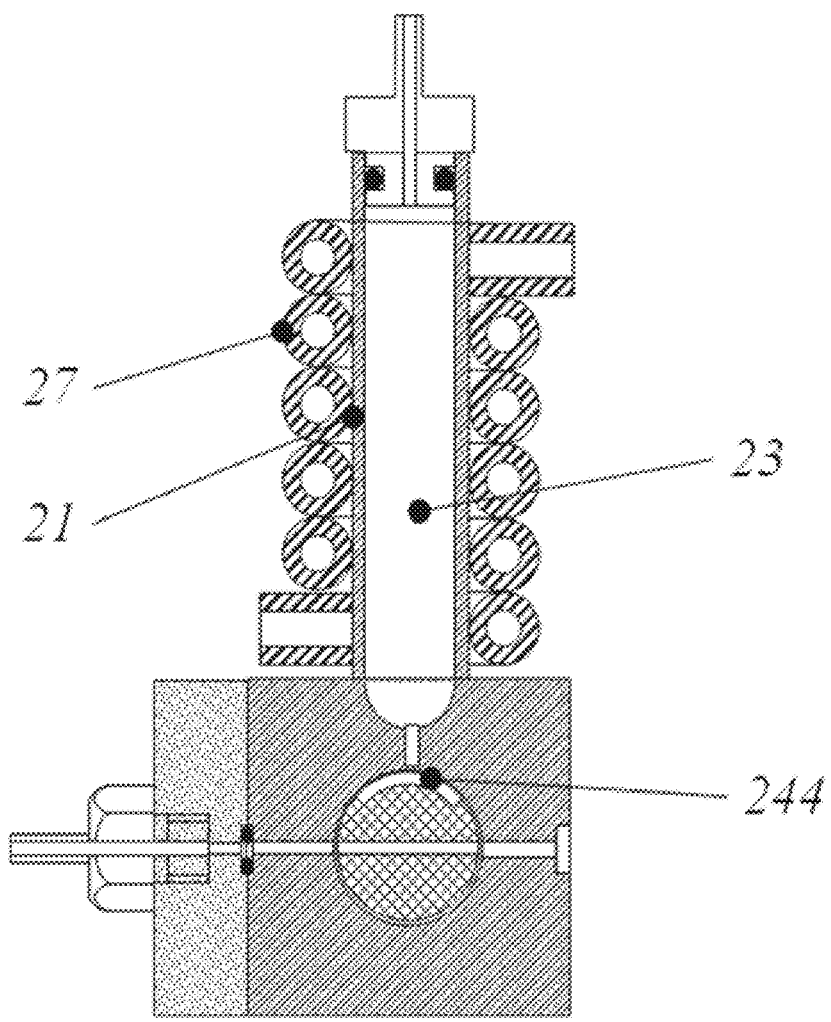
FIG. 10 is a structural diagram of an outer wall surrounded by a spiral guide pipe in an embodiment of the disclosure.

Another solution of heating or cooling the culture chamber 23 is shown in FIG. 10. A spiral guide pipe 27 surrounds the outer wall 21, and the heated or cooled liquid flows inside the spiral guide pipe 27. The inner diameter of the spiral guide pipe 27 is slightly smaller than the outer diameter of the culture chamber 23, so the spiral guide pipe 27 will be tightly attached to the outer wall 21. When the spiral guide pipe 27 needs to be removed, the spiral guide pipe 27 needs to be slightly loosened so as to increase the inner diameter thereof.

Figure 11:
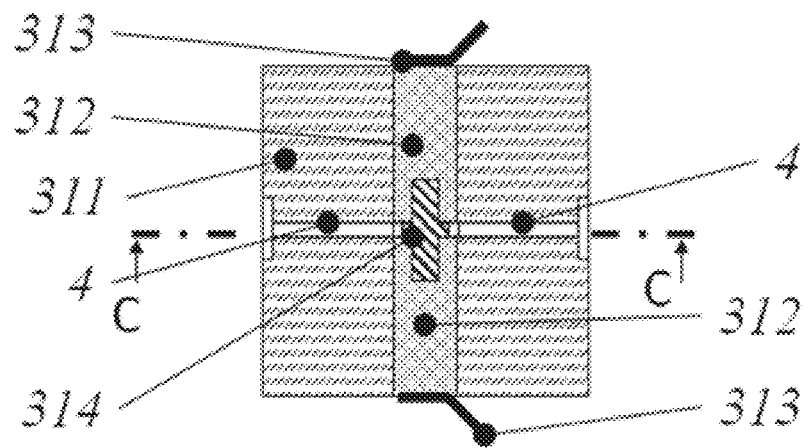
FIG. 11 is a structural diagram of an electric treatment compartment in an embodiment of the disclosure.
Figure 12:
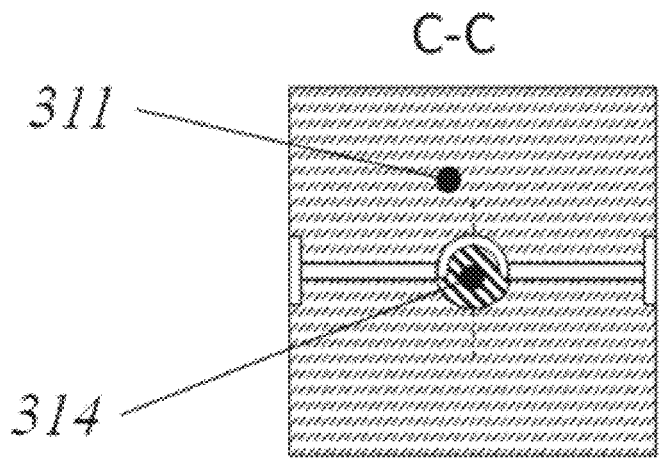
FIG. 12 is a section view of a part C-C in FIG. 11.
Figure 13:
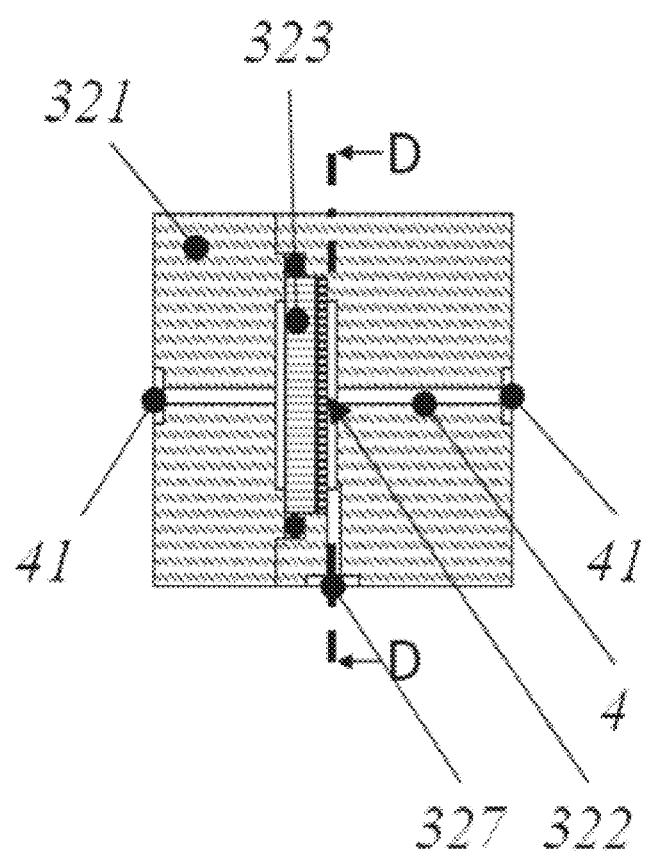
FIG. 13 is a structural diagram of a first filter compartment in an embodiment of the disclosure.
Figure 14:
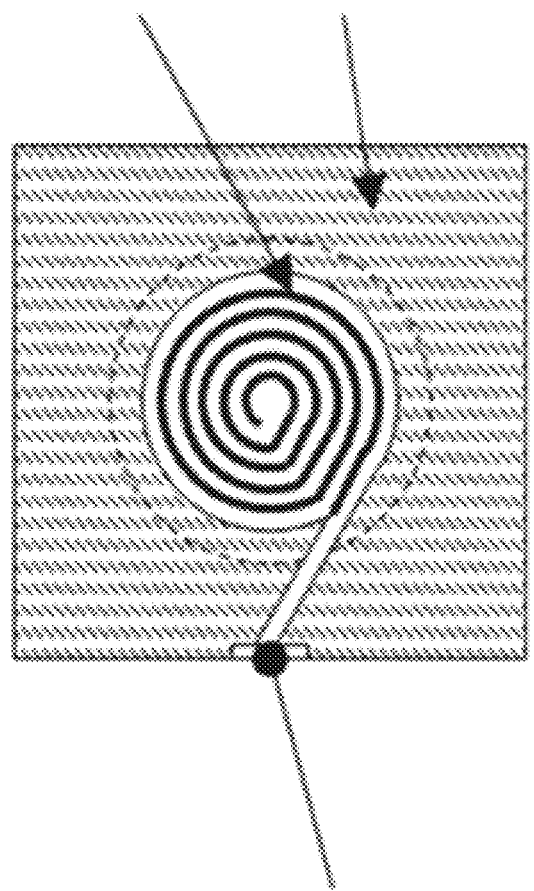
FIG. 14 is a section view of a part D-D in FIG. 13.
Figure 15:
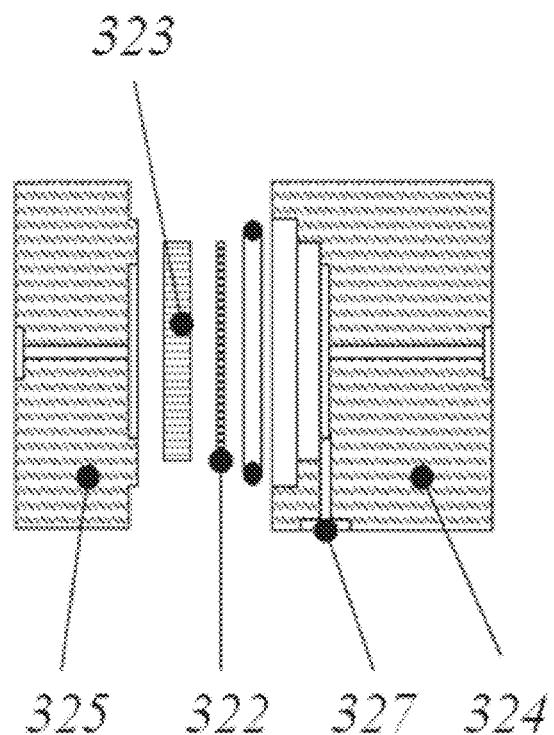
FIG. 15 is an explosive structural diagram of a filter compartment in an embodiment of the disclosure.

The treatment compartment 3 provided in the disclosure includes an electric treatment compartment, a filter compartment and a cell density measurement compartment, wherein with reference to FIG. 11 and FIG. 12, the electric treatment compartment includes a second standard shape block 311 which is provided with a pipeline 4 and can be connected to the mounting surfaces, two electrodes 312 face two sides of the pipeline 4 in the middle of the second standard shape block 311, and electric connectors 313 which can be connected to external power supplies are arranged at the outer ends of the two electrodes 312. Specifically, the second standard shape block 311 is made from an electric insulating material, and a cell suspension can be treated under an AC, a DC or a transient current or voltage. This may be used for measuring electric properties of the cell suspension or used for transitorily changing the characteristics of cells. For example, a transient high-voltage pulse may deliver macromolecules such as plasmids or oligonucleotides into the cells (electric transformation). When in use, the power supplies are connected to the electrodes 312 by means of the electric connectors 313, the cell suspension with a certain small volume will be located in an electric field between the two electrodes 312, and is continuously and electrically shocked. An electric shock frequency matches a flow speed of the cell suspension. In order to avoid accidental contact between the two electrodes 312, an insulating partition sheet 314 is arranged between the two electrodes 312 in the pipeline 4, and the insulating partition sheet 314 forms a protrusion controlling the liquid to flow through the pipeline 4.

The filter compartment provided in the disclosure is designed to include a first filter compartment and a second filter compartment. Specifically, with reference to FIG. 13, FIG. 14 and FIG. 15, the first filter compartment includes a third standard shape block 321 which is provided with a pipeline 4 and can be connected to the mounting surfaces, a filter device which divides the pipeline 4 into a front section and a rear section is arranged in the third standard shape block 321, the filter device includes a filter membrane 322 and a porous member 323 arranged at the rear side of the filter membrane 322, the third standard shape block 321 includes a front half part 324 and a rear half part 325 which can be assembled into a whole, an inner chamber for accommodating the filter device is formed between the front half part 324 and the rear half part 325, a first spiral guide groove 326 is formed in the end surface, tightly attached to the filter membrane 322, of the front half part 324, and a first port 327 for injecting external liquid is formed for the first guide groove 326 on the side surface of the front half part 324. When in use, the cell suspension flows through the filter membrane 322 and the porous member 323 by means of the pipeline 4, so as to deposit the cells on a residual liquid surface of the filter membrane 322. When the filter membrane 322 is replaced, the filter membrane 322 can be replaced by splitting the front half part 324 and the rear half part 325. After filtration, re-suspension of the cells may be implemented by means of two methods as follows.

(i) Fresh liquid may reversely press the filter membrane 322 from the reverse side of the filter membrane 322.

(ii) Fresh liquid may be injected from the first port 327, and the first spiral guide groove 326 will guide the fresh liquid to flow on the residual liquid surface of the filter membrane 322. It is important to note that the first port 327 needs to be connected to a valve and keeps closed in a filtration process. In this case, liquid in the cell suspension will penetrate through the filter membrane 322, and the cells will stay on the residual liquid surface of the filter membrane 322.

Figure 16:
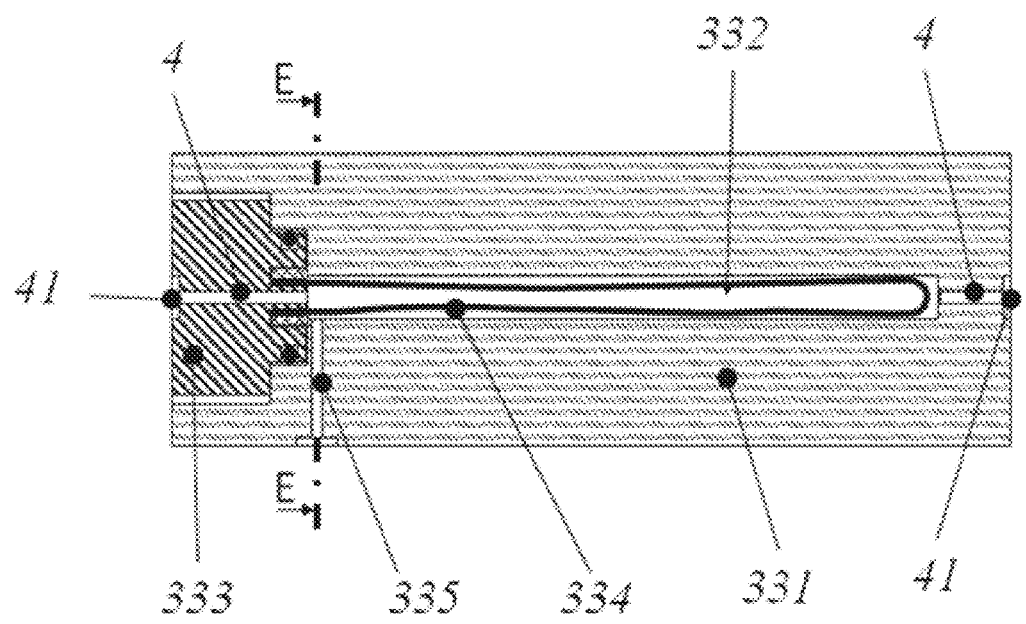
FIG. 16 is a structural diagram of a first embodiment for a second filter compartment in the disclosure.
Figure 17:
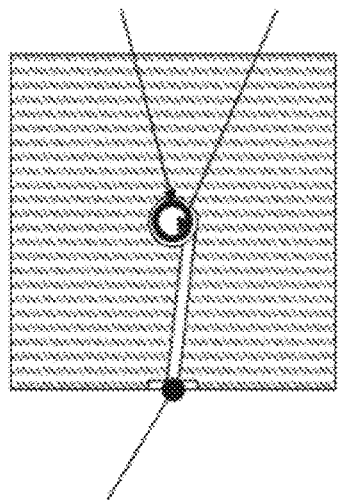
FIG. 17 is a section view of a part E-E in FIG. 16.

With reference to FIG. 16 and FIG. 17, the second filter compartment includes a fourth standard shape block 331 which is provided with a pipeline 4 and can be connected to the mounting surfaces, an inner filter chamber 332 communicated with a pipeline 4 is formed inside the fourth standard shape block 331, an end cap 333 which is hermetically connected to the fourth standard shape block 331 and is internally provided with a pipeline 4 is arranged at the tail end of the inner filter chamber 332, a fibre filter membrane 334 extending into the inner filter chamber 332 is arranged at the inner end of the end cap 333, a second port 335 communicated with the inner filter chamber 332 is provided on the side wall of the fourth standard shape block 331, and the second port 335 leads into the inner filter chamber 332 along a tangential direction. The inner end of the end cap 333 forms a cylindrical protrusion. The cylindrical protrusion is sheathed by the fibre filter membrane 334, and the fibre filter membrane 334 is fixed and sealed by resin. The end cap 333 integrally seals the tail end of the inner filter chamber 332 by means of an elastic sealing element. The cell suspension enters the inner filter chamber 332, and flows along the outer side of the fibre filter membrane 334. By designing the outer diameter of the inner filter chamber 332 to be slightly larger than that of the fibre filter membrane 334, spacing between the inner filter chamber 332 and the fibre filter membrane 334 can be controlled to be very small. While the cells are deposited on the outer side of the fibre filter membrane 334, the liquid will penetrate through the fibre filter membrane 334 and flow out from the pipeline 4 of the end cap 333. For the second filter compartment, there are two methods for re-suspending the cells on the outer side of the fibre filter membrane 334. (1) Fresh liquid is injected from the end cap 333 and reversely presses the fibre filter membrane 334. (2) Fresh liquid enters the inner filter chamber 332 from the second port 335 along the tangential direction so as to generate circulation facilitating cell re-suspension.

Figure 18:
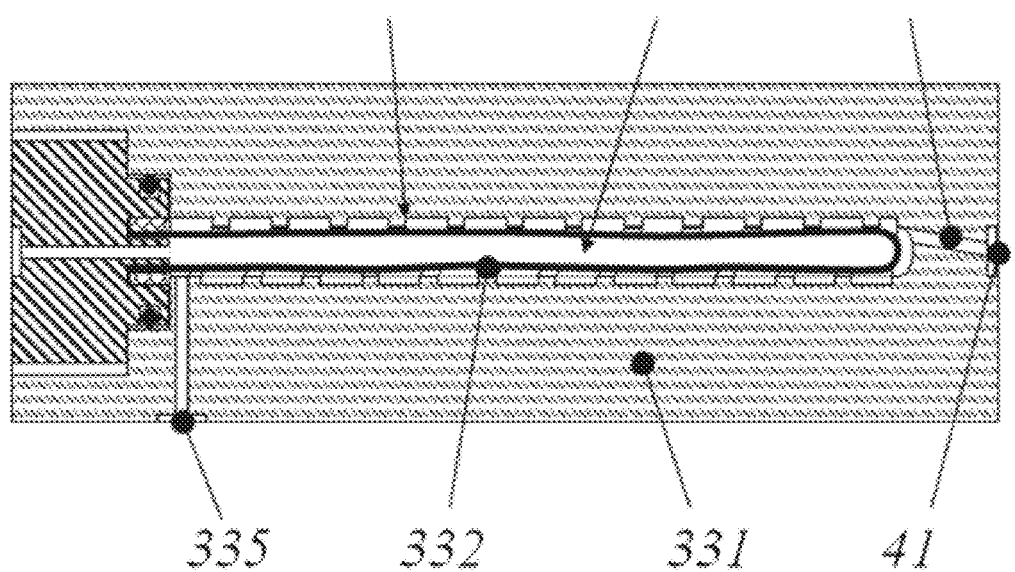
FIG. 18 is a structural diagram of a second embodiment for a second filter compartment in the disclosure.

With reference to FIG. 18, as a further improvement, in the second filter compartment, a second spiral guide groove 336 is provided on the inner wall of the inner filter chamber 332, and the second guide groove 336 and the second port 335 are connected and surround the fibre filter membrane 334. When the cells are re-suspended, fresh liquid will flow along the second spiral guide groove 336 and re-suspend the cells. Similarly, by controlling the inner diameter of the second spiral guide groove 336, the whole second filter compartment may be kept in small volume.

Figure 19:
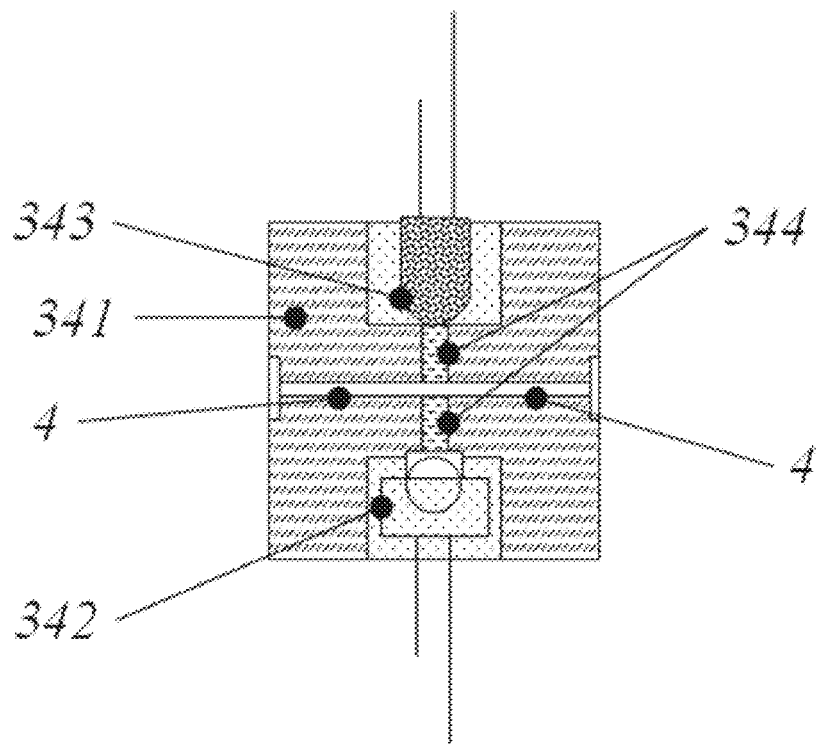
FIG. 19 is a structural diagram of a first embodiment for a cell density measurement compartment in the disclosure.

With reference to FIG. 19, the cell density measurement compartment includes a fifth standard shape block 341 which is provided with a pipeline 4 and can be connected to the mounting surfaces, an optical channel transversely penetrating through the pipeline 4 is provided on the fifth standard shape block 341, a light source 342 and a light sensor 343 are arranged at two ends of the optical channel respectively, and transparent waveguide elements 344 are arranged on two sides of the pipeline 4 between the light source 342 and the light sensor 343. Specifically, light emitted by the light source 342 (which may be a light emitting diode) passes through one transparent waveguide element 344, interacts with the cell suspension, is received by the other transparent waveguide element 344, and then reaches the light sensor 343 (phototransistor). The cell density measurement of the cell suspension is further completed.

Figure 20:
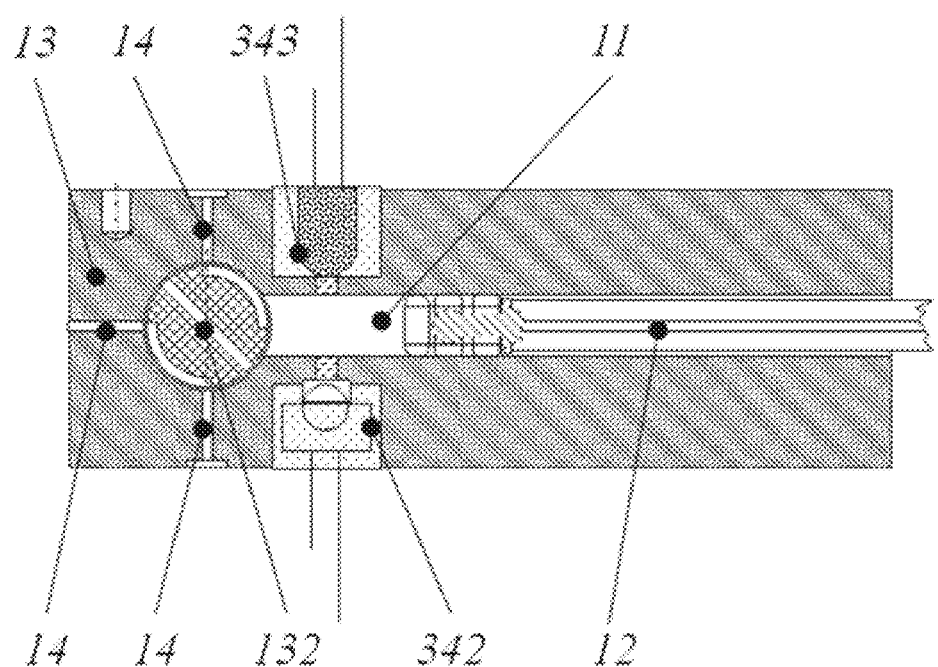
FIG. 20 is a structural diagram of a second embodiment for a cell density measurement compartment in the disclosure.

As shown in FIG. 20, the cell density measurement compartment and the central distribution compartment 1 are arranged integrally, that is, an optical channel transversely penetrating through the distribution chamber 11 is provided on the central distribution compartment 1, such that a light source 342 and a light sensor 343 are located at positions, on two sides of the distribution chamber 11, in the optical channel, and transparent waveguide elements are arranged on two sides of the distribution chamber 11 between the light source 342 and the light sensor 343. The design reduces liquid amount needed during cell density measurement, and reduces needed mechanical motions. Once connection is established between the culture compartment 2 and the central distribution compartment 1, after the cells reach the distribution chamber 11, cell density can be directly measured. Besides, because the distribution chamber 11 has a larger diameter, the quantity of the measured cells is larger, and a measurement result is more accurate.

Figure 21:
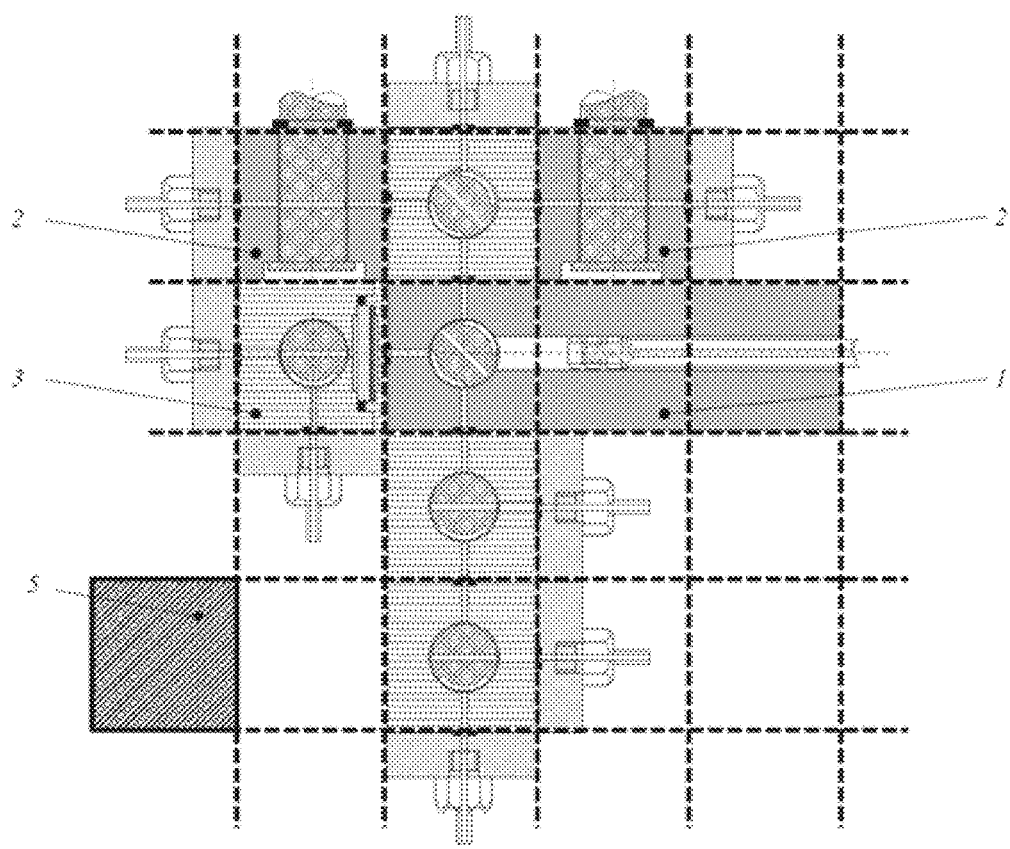
FIG. 21 is a diagram of an idea of adopting a general shape block as a standard shape block in the disclosure.

To enable an experimenter to freely select a compartment to mount the device according to an experiment flow, a standard shape block having a general shape 5 is adopted in the disclosure as a basis to be applied to a culture compartment 2, a central distribution compartment 1 and all treatment compartments 3. Imprints of the culture compartment 2, the central distribution compartment 1 and all the treatment compartments 3 can be regarded as multiples of the general shape 5, and therefore the culture compartment 2, the central distribution compartment 1 and all the treatment compartments 3 are easily combined into different configurations. FIG. 21 shows a design idea, the general shape 5 is represented by a square. The device shown in FIG. 21 includes two culture compartments 2, a central distribution compartment 1, a treatment compartment 3 and three valves. Imprints of the central distribution compartment 1 can be regarded as three general shapes 5. Besides, the imprints of all compartments are equal to a general shape.

Figure 22:
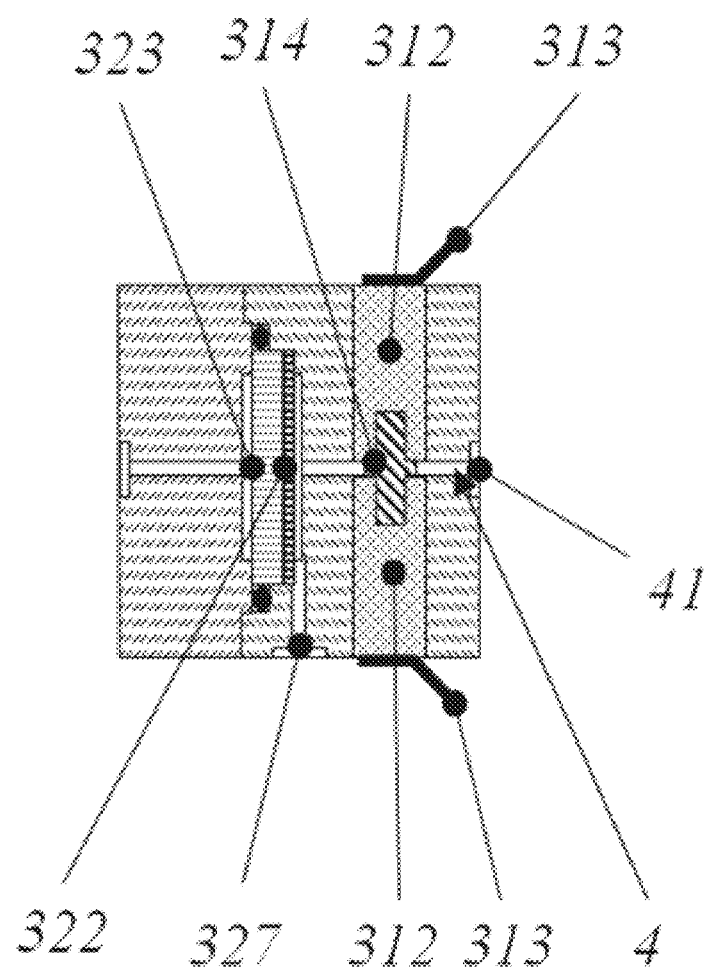
FIG. 22 is a structural diagram of a composite treatment compartment in the disclosure.

FIG. 22 shows a composite treatment compartment. An electric treatment compartment and a first filter compartment described above are combined in a standard shape block. The combination has the advantages that the suspension volume of a pipeline 4 is reduced to the greatest extent, and the combination matches the design of the general shape 5.

With reference to FIG. 1, in order to connect two adjacent compartments, external outlets of pipelines 4 of different compartments will be aligned along with self-border alignment of the compartments. Grooves 41 are provided around the external outlets of the pipelines 4 of different compartments, and sealing elements are arranged in the grooves 41 and are configured to seal the pipelines 4 between the compartments so as to prevent liquid from leaking at a joint.

In order to guarantee that two adjacent compartments are completely aligned, a matching hole 43 is provided on each compartment, and can realize perfect connection by means of a simple connector element 44, wherein the connector element 44 may adopt a simple cylindrical pin or flat key.

Certainly, the creation of the disclosure is not limited to the above implementation, those skilled in the art can also make equivalent deformations or replacements without departing from the spirit of the disclosure, and these equivalent deformations or replacements fall within the scope limited by the claims of the present application.

What is claimed is:

1. A cell culture and experiment device, comprising: a central distribution compartment, a culture compartment, a treatment compartment, and pipelines for delivering liquid between the central distribution compartment and the culture compartment and between the central distribution compartment and the treatment compartment, wherein a distribution chamber and a piston capable of moving back and forth in the distribution chamber to change the working volume of the distribution chamber are provided in the central distribution compartment, and a distribution valve for controlling the distribution chamber to be communicated with any pipeline is arranged at the bottom end of the distribution chamber in the central distribution compartment, wherein the central distribution compartment, the culture compartment and the treatment compartment are arranged separately, the central distribution compartment surrounds the distribution valve to form a plurality of mounting surfaces which can be connected to the culture compartment or the treatment compartment, a central pipeline leading from the distribution valve to each mounting surface is arranged on the central distribution compartment, the distribution valve comprises a central cylinder hole provided at the bottom end of the distribution chamber and a central valve element which is inserted into the central cylinder hole and can rotate in the central cylinder hole, a central flow channel is provided on the central valve element, and when the central valve element rotates, the central flow channel can communicate the distribution chamber with any central pipeline, wherein the culture compartment comprises a culture chamber formed by a cylindrical outer wall and a plug arranged at the front end of the outer wall, and a multi-way valve arranged at the rear end of the outer wall; an air hole is provided on the plug; the multi-way valve comprises a first standard shape block which can be connected to the mounting surfaces and is provided with a cylinder hole and a pipeline, and a first valve element which is inserted into the cylinder hole and can rotate in the cylinder hole; a first connector is arranged on the first standard shape block; a first flow channel is provided on the first valve element; and when the first valve element rotates, the first flow channel can communicate the first connector with the culture chamber by means of the pipeline or communicate the first connector with the distribution valve or communicate the culture chamber with the distribution valve.

2. The cell culture and experiment device according to claim 1, wherein the outer side of the outer wall is sheathed by a sleeve, a cavity is formed between the sleeve and the outer wall, an outlet and an inlet communicated with the cavity are formed at the front end and rear end of the sleeve, and a spiral partition wall is arranged in the cavity so as to form a channel which surrounds the outer wall and is connected to the outlet and the inlet.

3. The cell culture and experiment device according to claim 1, wherein a spiral guide pipe surrounds the outer wall, and the inner diameter of the spiral guide pipe is smaller than the outer diameter of the culture chamber.

4. The cell culture and experiment device according to claim 1, wherein the treatment compartment comprises an electric treatment compartment, the electric treatment compartment comprises a second standard shape block which is provided with a pipeline and can be connected to the mounting surfaces, two electrodes face two sides of the pipeline in the middle of the second standard shape block, electric connectors which can be connected to external power supplies or measurers are arranged at the outer ends of the two electrodes, an insulating partition sheet is arranged between the two electrodes in the pipeline, and the insulating partition sheet forms a protrusion controlling liquid to flow through the pipeline.

5. The cell culture and experiment device according to claim 1, wherein the treatment compartment comprises a first filter compartment, the first filter compartment comprises a second standard shape block which is provided with a pipeline and can be connected to the mounting surfaces, a filter device which divides the pipeline into a front section and a rear section is arranged in the second standard shape block, the filter device comprises a filter membrane and a porous member arranged at the rear side of the filter membrane, the second standard shape block comprises a front half part and a rear half part which can be assembled into a whole, an inner chamber for accommodating the filter device is formed between the front half part and the rear half part, a first spiral guide groove is formed in the end surface, tightly attached to the filter membrane, of the front half part, and a first port for injecting external liquid is formed for the first guide groove on the side surface of the front half part.

6. The cell culture and experiment device according to claim 5, wherein the treatment compartment comprises a second filter compartment, the second filter compartment comprises a third standard shape block which is provided with a pipeline and can be connected to the mounting surfaces, an inner filter chamber communicated with a pipeline is formed inside the third standard shape block, an end cap which is hermetically connected to the third standard shape block and is internally provided with a pipeline is arranged at the tail end of the inner filter chamber, a fibre filter membrane extending into the inner filter chamber is arranged at the inner end of the end cap, a second port communicated with the inner filter chamber is provided on the side wall of the third standard shape block, and the second port leads into the inner filter chamber along a tangential direction.

7. The cell culture and experiment device according to claim 6, wherein a second spiral guide groove is provided on the inner wall of the inner filter chamber, and the second guide groove and the second port are connected and surround the fibre filter membrane.

8. The cell culture and experiment device according to claim 1, wherein the treatment compartment comprises a cell density measurement compartment, the cell density measurement compartment comprises a second standard shape block which is provided with a pipeline and can be connected to the mounting surfaces, an optical channel transversely penetrating through the pipeline is provided on the second standard shape block, a light source and a light sensor are arranged at two ends of the optical channel respectively, and transparent waveguide elements are arranged on two sides of the pipeline between the light source and the light sensor.

9. The cell culture and experiment device according to claim 1, wherein an optical channel transversely penetrating through the distribution chamber is provided on the central distribution compartment, a light source and a light sensor are arranged at two ends of the optical channel respectively, and transparent waveguide elements are arranged on two sides of the distribution chamber between the light source and the light sensor.

* * * * *